United States Patent [19]
Raspino, Jr.

[11] Patent Number: 5,938,435
[45] Date of Patent: Aug. 17, 1999

[54] ORTHODONTIC APPLIANCE SHIELD SYSTEM

[76] Inventor: Jude G. Raspino, Jr., 3 Acadia St., Kenner, La. 70065

[21] Appl. No.: 08/898,210

[22] Filed: Jul. 22, 1997

[51] Int. Cl.⁶ ..................................................... A61C 3/00
[52] U.S. Cl. ................................................. 433/2; 433/22
[58] Field of Search ................................ 433/2, 8, 9, 11, 433/15, 22, 71

[56] References Cited

U.S. PATENT DOCUMENTS

| | | | |
|---|---|---|---|
| 2,183,624 | 12/1939 | Schwartz | 433/71 |
| 3,064,354 | 11/1962 | Pos | 433/71 |
| 3,372,484 | 3/1968 | Mumaw | 433/2 |
| 3,604,116 | 9/1971 | Shpuntoff | 433/71 |
| 4,512,740 | 4/1985 | Kurz | 433/8 |
| 4,527,975 | 7/1985 | Ghafari et al. . | |
| 4,559,013 | 12/1985 | Amstutz . | |
| 4,609,348 | 9/1986 | Rowland . | |
| 4,657,508 | 4/1987 | Dellinger | 433/9 |
| 4,913,654 | 4/1990 | Moraon et al. . | |
| 4,978,391 | 12/1990 | Jones | 433/8 |
| 5,037,296 | 8/1991 | Karwoski . | |
| 5,160,260 | 11/1992 | Chang . | |
| 5,299,936 | 4/1994 | Ueno | 433/71 |
| 5,324,348 | 6/1994 | Perret . | |
| 5,662,471 | 9/1997 | Fogerty | 433/2 |
| 5,707,235 | 1/1998 | Knutson | 433/213 |

FOREIGN PATENT DOCUMENTS 4103991  8/1992  Germany ................................. 433/48

OTHER PUBLICATIONS

John O. Butler Co., Chicago, IL, Butler GUM brand Orthodontic Wax, Mint Flavor Package. No Date.
Johnson & Johnson Consumer Products, Inc., Skillman NJ, FIRST AID brand sterile gauze pad package and pad No Date.
Imfalab, Inc., Brace Relief Leaflet No Date.

Primary Examiner—Ralph A. Lewis
Attorney, Agent, or Firm—Joseph T. Regard, Ltd

[57] ABSTRACT

A mouth shield system configured to protect the lips and tongue of a user from an installed orthodontic appliance, dental work, or the like. The preferred embodiment of the present invention comprises a strip formed from a light material such as, for example, mesh gauze, impregnated and surrounded by a plastic material such as, for example, dental wax or the like, the strip laminated on one outer side with a cover of, for example, cling wrap or the like. The strip is of an adequate width to envelope the raised portion of a dental appliance or other dental work, and of sufficient length preferably to cover the length of the appliance or dental work. In use, the user cuts the strip to the desired length so as to envelop the bracket and/or wire of the appliance, applying pressure to the strip and manipulating same so that it wraps about the exterior of the brackets, so as to allow the malleable properties of the strip to engage the brackets and retain the strip to same. The bracket and wires are then shielded from the inner lips of the user, and the user may enjoy foods and beverages as normal. The may be removed after eating for cleaning or brushing of the teeth, and replaced with a new strip when shielding is again desired. An alternative embodiment of the present invention contemplates the wax of the invention being infused with a breath freshener, fluoride, teeth whitener or medication, such as a topical anesthetic to relieve pain, an anticoagulant to prevent bleeding, or an antibiotic to prevent infection.

16 Claims, 5 Drawing Sheets

ORTHODONTIC APPLIANCE SHIELD SYSTEM

TECHNICAL FIELD OF THE INVENTION

The present invention relates to mouth guards, shields and the like, and particularly to a mouth shield system configured to protect the lips and tongue of a user from an installed orthodontic appliance, dental work, or the like. A further example of the present invention contemplates a shield which is affixed to an orthodontic appliance between the teeth and the lips, the shield configured to protect the inner lips and tongue of the user from orthodontic wires and brackets.

The preferred embodiment of the present invention comprises a strip formed from a light material such as, for example, mesh gauze, impregnated and surrounded by a plastic material such as, for example, dental wax or the like, the strip laminated on one outer side with a cover of, for example, cling wrap or the like.

The strip is of an adequate width to envelope the raised portion of a dental appliance or other dental work, and of sufficient length preferably to cover the length of the appliance or dental work. The laminate strip is ideally of sufficient thickness to allow the strip to bend about the dental work, while shielding and covering same.

In use, the user cuts the strip-to the desired length so as to envelop the bracket and/or wire of the appliance, applying pressure to the strip and manipulating same so that it wraps about the exterior of the brackets, so as to allow the pliable or mallaeble properties of the strip to engage the brackets and retain the strip to same. The bracket and wires are then shielded from the inner lips of the user, and the user may enjoy foods and beverages as normal. The strip is easily removed after eating for brushing the teeth, and replaced with a new strip when shielding is again desired. The strip may be removed for sleeping, if desired, although it is believed that the strip will remain intact during sleeping with most orthodontic appliances.

An alternative embodiment of the present invention contemplates the wax of the invention being infused with a breath freshener, fluoride, teeth whitener or medication, such as a topical anesthetic to relieve pain, an anticoagulant to prevent bleeding, or an antibiotic to prevent infection.

BACKGROUND OF THE INVENTION

Although the field of orthodontics has evolved considerably in recent years, an undesirable factor which continues to afflict its users is the pain and discomfort of wearing such a device, which affliction is particularly acute at the inception of treatment.

The prior art has contemplated various pads, shields and other apparatus, but none are believed to have offered the simplicity, comfort, cleanliness and relative ease of use as the system of the present invention.

A listing of patents which may have some pertinence to the field of dental shields, pads presented below:

| Patent Number | Inventor(s) | Date of Issue |
| --- | --- | --- |
| 5324348 | Perret | 06/28/1994 |
| 5160260 | Chang | 11/03/1992 |
| 5037296 | Karwoski | 08/06/1991 |
| 4913654 | Morgon et al | 04/03/1990 |
| 4609348 | Rowland | 09/02/1986 |
| 4559013 | Amstutz | 12/17/1985 |
| 4257975 | Ghafari et al | 07/09/1985 |
| 4512740 | Kurz | 04/23/1985 |

As may be discerned by a review of the above, the prior art recognizes the general concept of the utilization of shields to prevent injury from orthodontic appliances; as contemplated in U.S. Pat. No. 4,913,654 issued 1990, which teaches a plastic shield configured to engage the bracket and wire of the appliance.

U.S. Pat. No. 4,512,740 teaches another embodiment of a plastic shield, also configured to engage the brackets of an orthodontic appliance.

U.S. Pat. No. 5,037,296 teaches a "Lip Protector from Orthodontic Wires and Brackets", teaching a strip of pliable plastic or rubber configured to envelope the brackets and wire or an orthodontic appliance.

U.S. Pat. No. 4,609,348 teaches the utilization of foam resin shields for preventing injury from braces. See the discussion in Column 1, lines 16–26, which discusses the known utilization of many years of lengths of wax applied to the braces to shield same from the lips of the user.

U.S. Pat. No. 4,559,013 teaches an orthodontic shield utilizing silicone.

U.S. Pat. No. 4,527,975 and 5,160,260 teach caps which fit over the brackets of an orthodontic appliance.

U.S. Pat. No. 5,324,348 teaches a "Disposable Orthodontic Wire Marker" comprising a shaft made of stiff material coated on one end with a binder such as wax for marking metal wires.

The remaining patents teach various orthodontic shields, dams, sponges and the like, some of which are fabricated from gauze laminated with other materials, including U.S. Pat. No. 4,071,955 entitled "Highly Absorbent Sponge".

In summary, while the known prior art has contemplated several and diverse shields, guards, pads and the like for isolating an orthodontic appliance, shield, damaged teeth, or dental work from the flesh of the user, it is submitted that none have provided the simplicity, comfort, cleanliness and relative ease of use as the system of the present invention. As shown, plastic shields which are mechanically affixed to the orthodontic appliance may dislodge, and the edges of the shields themselves may be irritating to the tongue or gums of the user.

GENERAL SUMMARY DISCUSSION OF THE INVENTION

Unlike the prior art, the system of the present invention provides a system for enveloping and shielding an orthodontic appliance from the flesh of a user in a secure, comfortable, sanitary, in a relatively cost effective and easily maintained fashion.

As indicated, the present invention relates to a shield system configured to protect the lips and tongue of a user from an installed orthodontic appliance, dental work, or the like, in the form of a shield formed from material which is affixed to an orthodontic appliance between the teeth and the lips, thereby shielding the inner lips and tongue of the user from orthodontic wires, brackets, dental work, broken teeth or other irregular, pointed, or jagged surface.

The preferred embodiment of the present invention comprises a strip having therein a light material such as, for example, mesh gauze, impregnated and surrounded by a pliable material such as, for example, dental wax or the like, the strip further having disposed on an outer side a cover of thin film plastic wrap or the like, forming a laminate strip of pliable material having an outer smooth surface and an inner mesh for strength, durability, and pliability.

The preferred embodiment of the invention contemplates strip is of an adequate width to envelope the raised portion of a dental appliance or other dental work, and of sufficient length preferably to cover the length of the appliance or dental work. Ideally, the laminate strip is of sufficient width and thickness to allow the body of the strip to bend about the dental work to engage and cover the edges and cover or fill voids, providing an removable anchoring of the strip about the dental work, while shielding and covering same.

In use, the user cuts the strip to the desired length so as to envelop the bracket and/or wire of the appliance, applying pressure to the strip and manipulating same so that it wraps about the exterior of the brackets, so as to allow the plastic properties of the strip to engage the brackets and retain the strip to same. Because the present invention contemplates the utilization of dental wax as the main material, it may be necessary to warm the wax between the hands of the user, or in a warm cup of water prior to application, to provide a soft, pliable material for application. After enveloping the appliance with the strip, inner lips of the user are shielded from the rough surfaces thereof, and the user may enjoy foods and beverages as normal. As indicated, the strip may be removed after eating for cleaning of the teeth, and replaced with a new strip when shielding is again desired.

An alternative embodiment of the present invention contemplates the wax of the invention being infused with a breath freshener, fluoride, teeth whitener or medication, such as a topical anesthetic to relieve pain, an anticoagulant to prevent bleeding, or an antibiotic to prevent infection.

An important feature of the lamination of the present invention is that it provides the soft, sanitary shielding of the rough areas of dental wax, but without the need for forming, application, re-application, and picking out of residue once removed. Only plain dental wax, the laminate of the present invention, with the mesh infused therein, provides a means to hold the structure together during application and removal, while providing a means of strengthening the laminate to discourage unintended loosening of the shield by talking, eating, or other activities. Further, the thin film plastic sheeting covering the outer side of the strip provides a smooth surface to interface with the tissue of the user, while enclosing and locking in the wax or like material forming the body, preventing breakup and dislodging into the mouth of pieces of body material, while shielding the inner wax from food particles and preventing unintended removal of same.

It is therefore an object of the present invention to provide a shield for an orthodontic appliance comprised of soft, pliable material, which remains securely in place as installed, but is easily removable in its entirety.

It is another object of the present invention to provide a system for shielding a user's mouth tissues from sharp, abrasive, or rough surfaces, in a manner which is safe, relatively inexpensive, and effective in operation.

It is another object of the present invention to provide a system for shielding a user's mouth tissues from sharp, abrasive, or rough surfaces with a shielding material which also has infused therein for slow release a breath freshener, tooth whitener, tooth strengthener such as fluoride, or medication such as anti-coagulant, anti-biotic, analgesic, topical anesthetic, or the like.

Lastly, it is an object of the present invention to provide a system for shielding the mouth of a user utilizing a laminate strip which is designed to envelope a rough, abrasive, or sharp surface, shielding the inner mouth tissues of the user.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein.

DETAILED DISCUSSION OF THE INVENTION

Figure 3:
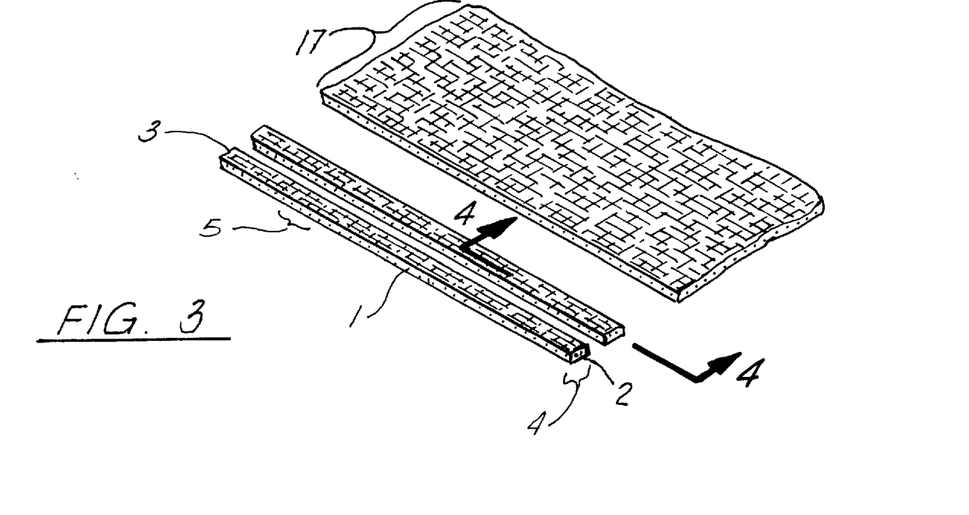
FIG. 3 is an isometric view of the fabrication of the dental shield of FIG. 1, illustrating the slicing of longitudinally aligned strips from the prepared batch, forming the individual dental shields.
Figure 4:
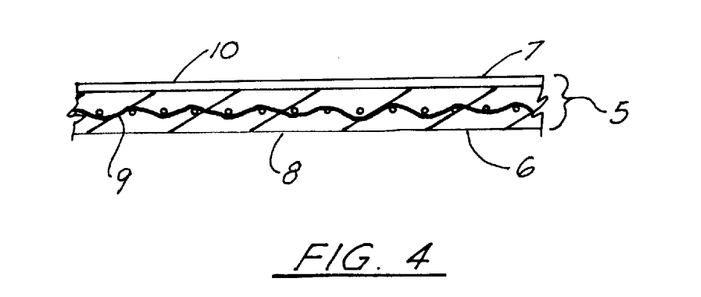
FIG. 4 is a cross-sectional view of the dental shield of FIG. 1, illustrating an example of the mesh having the dental wax disposed thereabout, and the thin film plastic forming an outer surface.

Referring to FIGS. 3 and 4 of the drawings, the preferred embodiment of the orthodontic appliance shield of the present invention comprises a laminate strip 1 having first 2 and second 3 ends, a width 4, a thickness 5, and bottom 6 and top 7 faces, respectively. The strip body is formed of a pliable material 8 such as, for example, dental wax or the like, the strip further having situated therein a layer of mesh 9 such as, for example, a single layer of mesh material as distributed by Johnson & Johnson of Skillman, N.J. and utilized in its "First Aid" large sterile gauze pad, or the like, which is indicated as being of a rayon/cellulose composition. Cotton or other material, including material not particularly of a mesh configuration, such as, for example, fabric of varioius weaves may work with satisfactory results; the important thing is to provide a material which reinforces the wax or like material forming the body of the strip. It is envisioned that two or more plies of mesh material may be incorporated into the present system, depending upon the use, when a heavy-duty application is contemplated.

While dental wax is the preferred material for forming the body of the strip at this time, it is noted that other waxes and polymer products may be equally suitable. Preferably, the material should be non-flowing, but nonetheless somewhat pliable at an slightly elevated temperature to room temperature, which may include body temperature, having a melting point at least generally above 110 degrees, and should be substantially non-water soluble to avoid deterioration in the mouth of the user. Such a material may include, for example, a silicone or polymer based material, paraffin wax, or other substance.

Situated along the top face 7 of the strip is a smooth, preferably fluid impermeable, thin film material such as, for example, food grade plastic sheet wrap product; the preferred embodiment of the invention currently utilizes product bearing the trademark SARAN WRAP, manufactured by Dow Chemical, Inc, which is measured to be about 0.5 mm in thickness. It is noted that other thin film sheet product, including competing products known as "cling wrap" may be utilized, but has not found to date to provide as satisfactory results as the SARAN WRAP. Also, it is anticipated that a non-toxic polymer coating applied directly to the top face of the strip in liquid form and dried or cured may also provide the desired results. Ideally the product should cling to the dental wax or other material forming the pliable surface and provide a smooth contact area with the user's mouth tissue. A TEFLON coating may be utilized with or in lieu of the thin film.

An exemplary measurement of the strip 1 of the preferred embodiment of the present invention is about 4 inches long, by 0.25–0.33 inches wide, by ⅛ inches thick, although other measurements may be utilized, and the present, exemplary measurement may be trimmed as desired for use in different situations and appliance sizes.

Figure 1:
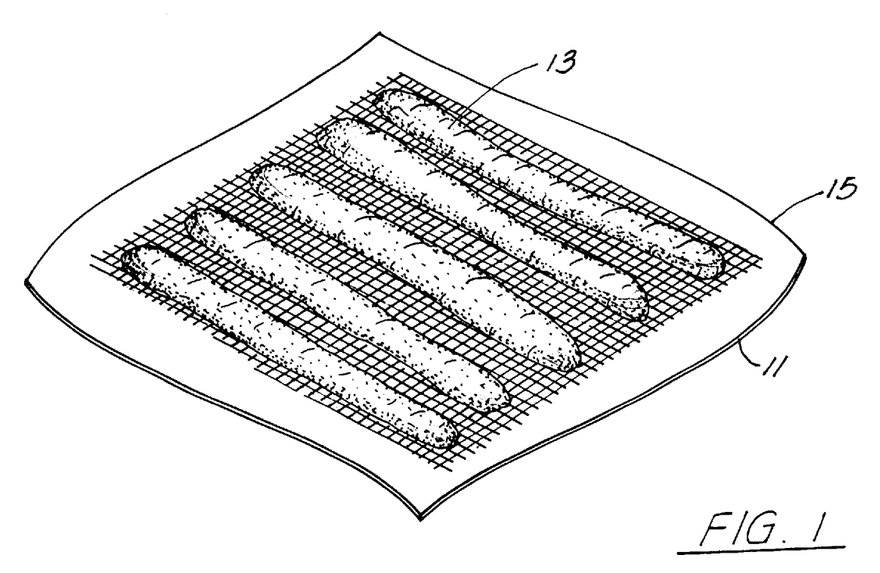
FIG. 1 is an isometric view of an exemplary fabrication of the dental shield of the present invention, illustrating a mesh having applied thereon a pliable material described in the preferred embodiment as dental wax.
Figure 2:
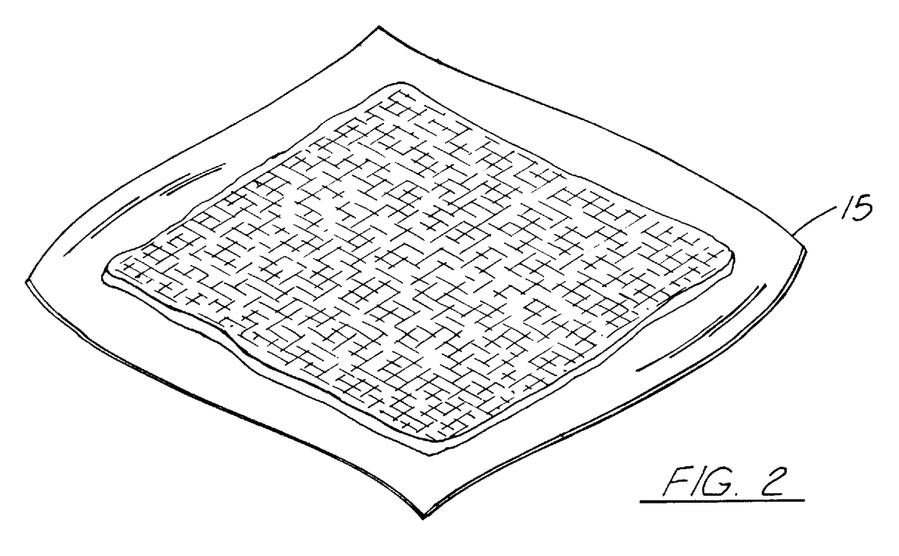
FIG. 2 is an isometric view of the fabrication of the dental shield of FIG. 1, illustrating the curing of the applied dental wax, and the application of thin film plastic thereupon, forming a covered surface.

FIGS. 1 and 2 illustrate an exemplary method of manufacture of the strip of the present invention. As shown, a square of thin film plastic material 15 is laid flat upon a non-stick, preferably heated surface or area (the preferred embodiment was made heating the surface via double boiler) in a single layer. Laid thereupon is a single sheet of gauze mesh 11 forming a plurality of threaded squares (the exemplary mesh currently utilized having formed therein about 330 squares per inch), which is shown having the exemplary measurement of four inches by four inches (4"×4"). In order to facilitate further flattening of the mesh and thin film plastic, the periphery may be flattened and spread by a stitch hoop, double hoop, or like structure. The pliable material 13 of the preferred embodiment of the invention is dental or orthodontic wax, such as that sold in block form and manufactured by John O. Butler Company, Chicago, Ill. under the trademark GUM is placed 12 in upon the mesh 11, thereafter heating the film, mesh, and wax or other material together until the wax or other material melts, for example, about 250 degrees, melting the material 13 and allowing same to infuse with the mesh and communicate with the thin film plastic material 15. If desired, the edges of the mesh and/or film may be framed by a container so as to allow the wax to be applied to the mesh 11 to a uniform desired thickness, for example, about ¼–1/16"; the exemplary thickness is ⅛". Other sizes and thicknesses may be implemented, depending upon the application. Upon melting and communication with the mesh, the mesh becomes infused within the wax, becoming suspended within same. The temperature mentioned is for exemplary purposes, and may vary with the materials implemented.

The product is then allowed to cool to generally about room temperature, forming a cake of shield material. As indicated, the present embodiment of the invention utilizes a thin film wrap, but future embodiments may incorporate a polymer or other coating which has like effect; in such a case, it may not be necessary to apply such coating while the wax or like body material is warm.

Once cooled to a pliable consistency, the laminate may be rolled under a rolling pin or the like or otherwise pressured to further solidify, strengthen, and provide a uniform thickness.

Alternatively, the mesh may be laid upon a flat surface, the material may be melted and infused with the mesh, and the thin film wrap may be applied thereupon.

Lastly, referring to FIG. 3, the prepared cake of shield material 17 is then sliced in longitudinally aligned strips of, for example, about ⅓–¼ inch, providing from a 4"×4" cake generally from about 12–16 strips.

Figure 7:
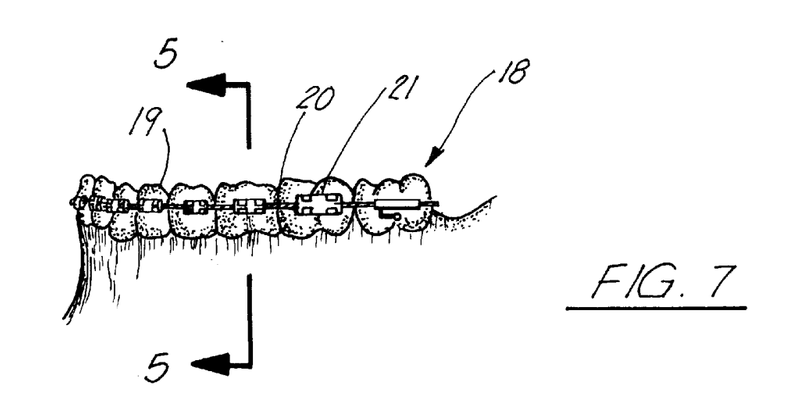
FIG. 7 illustrates a side view of the invention of FIG. 5.
Figure 9:
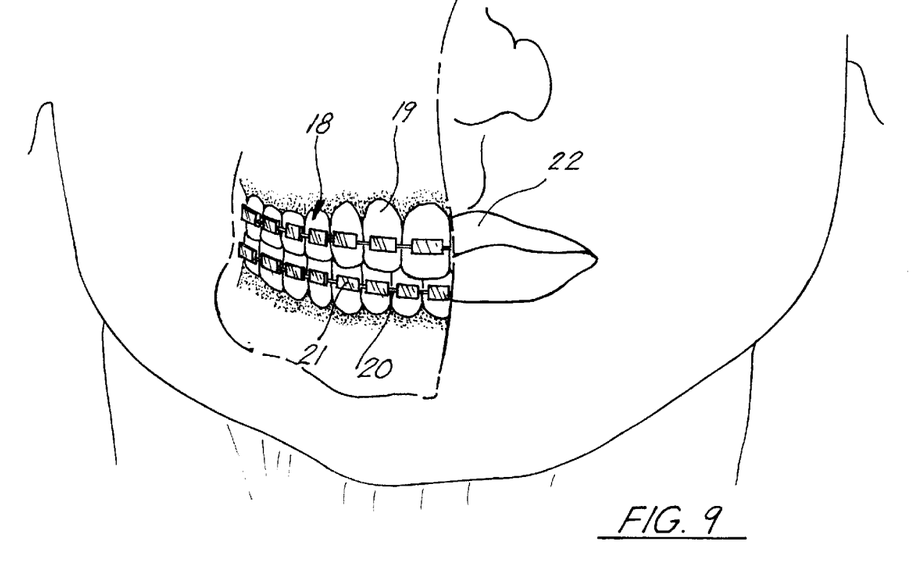
FIG. 9 illustrates a frontal, partially cut-away view of an exemplary user's mouth having dental work in the form of an orthodontic appliance installed thereupon.
Figure 11:
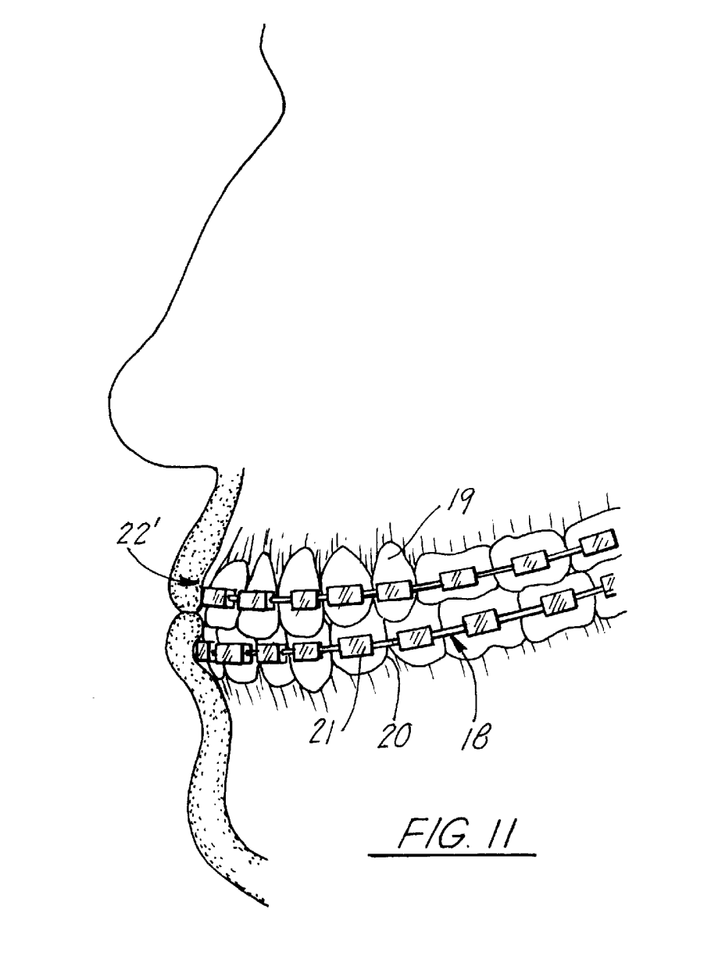
FIG. 11 illustrates a side, partially cut-away view of an exemplary user's mouth having thereupon dental work in the form of an orthodontic appliance.

Referring to FIGS. 7, 9, and 11, the strips of the present invention are useful for shielding the tissues 22', 22 of the mouth when rough or sharp edges are present therein, and appear at this time to be best suited for enveloping the wire 20 mounting brackets 21 of an orthodontic appliance 18 mounted to a users teeth 19 or the like, which tend to have sharp edges which cause discomfort and bleeding to the cheek tissues and tongue of the user contacting said brackets.

Figure 8:
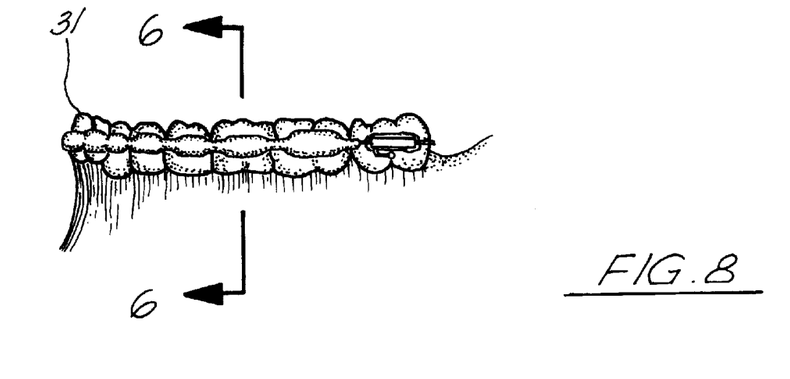
FIG. 8 is a side view of the invention of FIG. 6.
Figure 12:
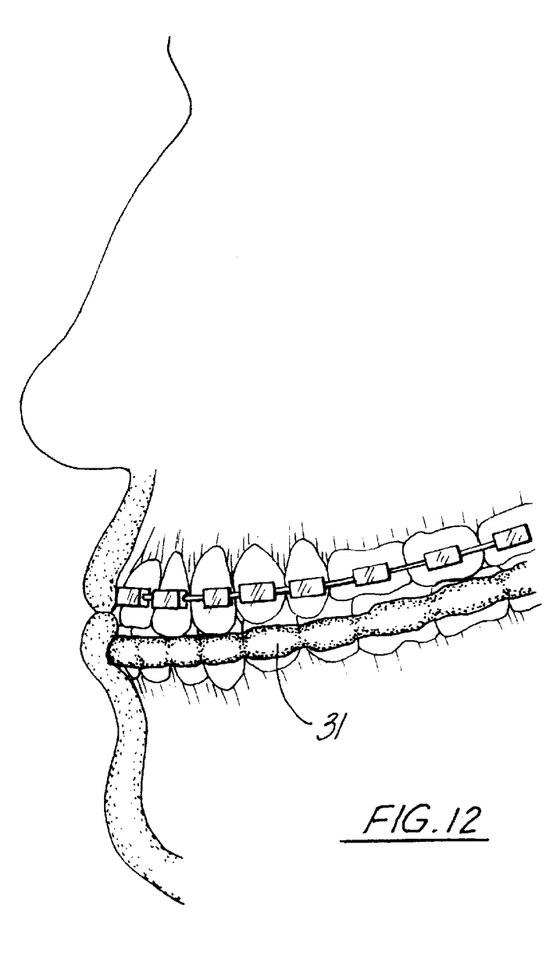
FIG. 12 illustrates the prepared strip of the present invention applied to lower dental work in the form of an orthodontic appliance, enveloping same, and protecting the inner lips and associated communicating tissues of the user.

Referring to FIGS. 8 and 12, the strip of the present invention is configured to engage and envelope 31 an irritating bracket or brackets forming an orthodontic appliance, or entire appliance (as shown) in an easily applied, yet easily removable fashion, protecting the mouth tissues of the user, while preventing the lodging of food in the appliance, etc.

Figure 5:
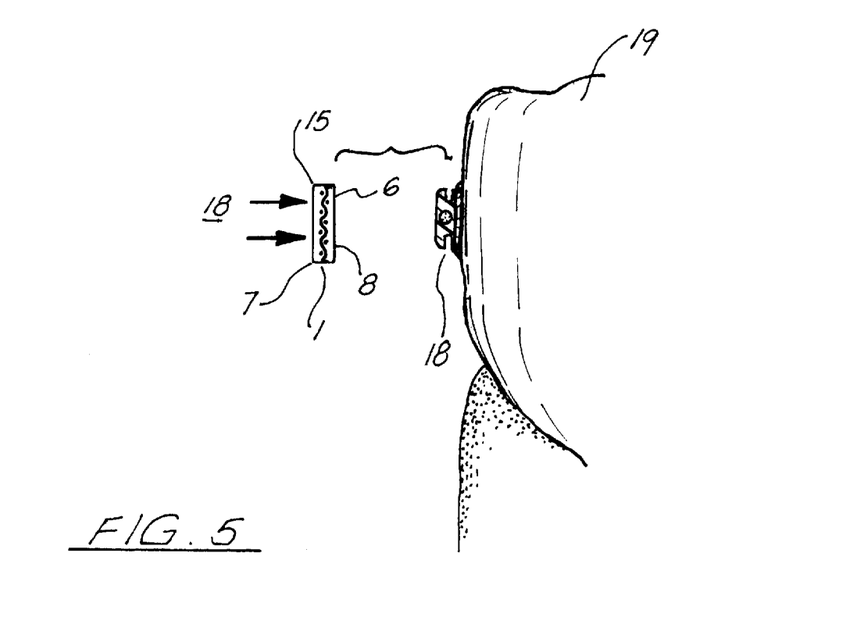
FIG. 5 is an end, partially cross-sectional view of the dental shield of FIG. 1, illustrating the end of the prepared strip being applied to dental work on the user's teeth.
Figure 10:
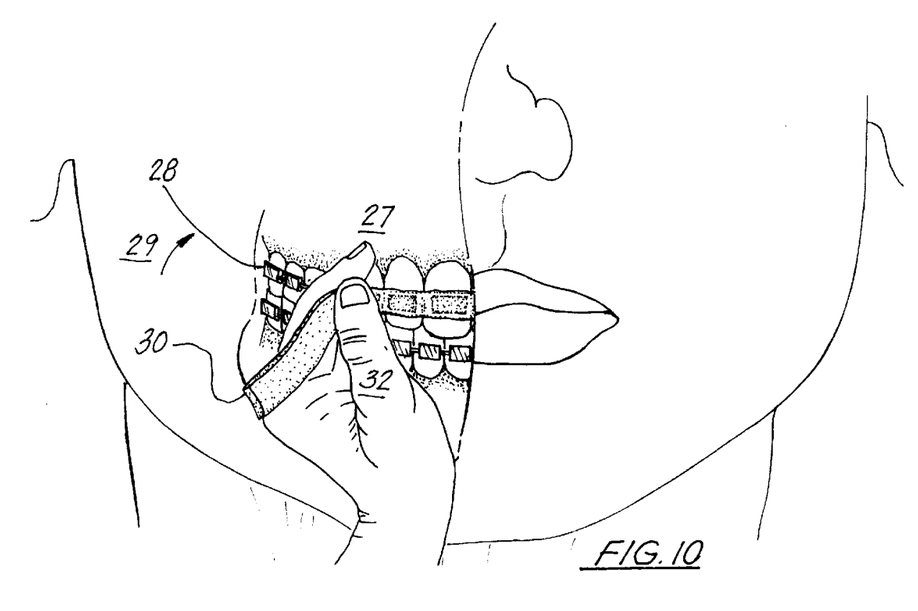
FIG. 10 illustrates a frontal, partially cut-away view of an exemplary installation of the prepared strip forming a dental shield, wherein the user applies the prepared strip to the dental work.

In use, referring to FIGS. 5 and 10, a strip 1 is longitudinally aligned with an orthodontic appliance 18, such that the bottom face 6 faces the appliance, the top face 7 is opposite the appliance, with the smooth thin film material 15 covering the top face likewise distal the appliance. One may trim the length of the strip to correspond generally to the length of the appliance, and may measure the appropriate length by placing one end of the strip against one end of the appliance, aligning and pressing the bottom face of the strip against the appliance along the length, applying light pressure to form an indentation in the wax forming the bottom face from the appliance along the length, removing the strip, noting where the indentations cease, and trimming accordingly.

As indicated, in use, the strip I is longitudinally aligned 27 with the appliance 18, with preferably one end of the strip being placed over one end of the appliance, with the strip applied 18' along the length 29, with the unattached end 30 of the strip being placed 32 over the hereto uncovered end 28 of the appliance. In situations where the air is cool, or a body material is utilized which is substantially rigid at body temperature, it may desirable to warm the strip in warm water or the like, to promote pliability of the wax or other material forming the body of the strip; the strip, once warmed, would be installed to envelope the area to be covered; once cooled to body temperature, the material would become more rigid, preventing loosening of same during use. Under such a scenario, it might be necessary to gargle with warm water to loosen the strip prior to removal.

Figure 6:
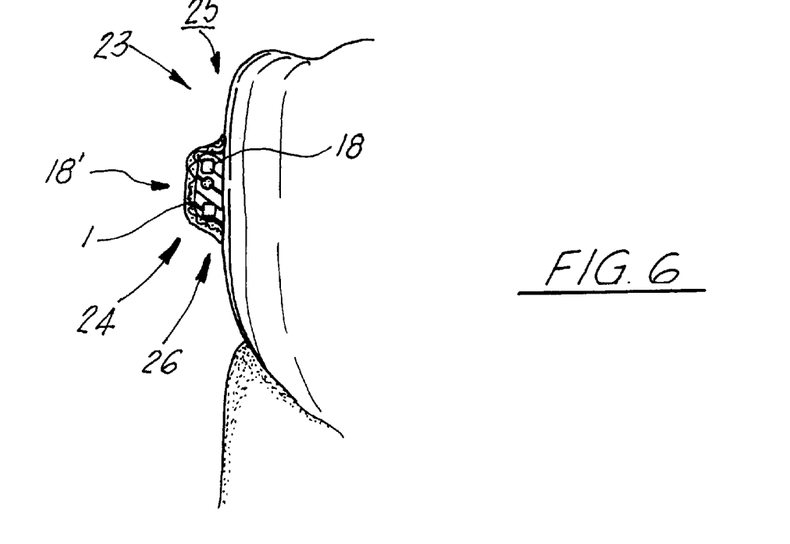
FIG. 6 is an end, partially cross-sectional view of the dental shield of FIG. 1, illustrating the prepared strip having been molded about the dental work, enveloping same.

Referring to FIG. 6, as the strip is placed upon the appliance, pressure 18' is exerted towards the appliance to meld a portion of the wax forming the bottom face into the appliance, while the longitudinal edges of the strip are likewise pressed 22, 24 against the appliance, effectively enveloping the upper 25 and lower 26 edges of the appliance, thereby encasing the appliance in the smooth, relatively inert material, forming the top face, shielding the user's tissues from jagged edges, wires, etc. of the appliance. As shown, the malleable material not only envelopes the appliance, it also is received by voids in the appliance, further anchoring the strip to same.

Once installed, the present invention protects the user's inner lip, tongue and tissues from abrasion, even during eating, as said tissues communicate with the smooth top face, and the sharp edges of the appliance are isolated in the body of the strip.

The construction of the present invention is such that wax forming the body of the strip will not become dislodged, due to the laminate construction, and tests have confirmed that the system, once installed, has yet to dislodge without the user actively seeking to remove same. Nonetheless, once the user desires to remove the strip, the strip is merely grasped by the user and peeled from the appliance. The laminate construction prevents wax from retaining to the appliance, allowing the user to easily remove the strip for teeth cleaning, examination, or other activities. The strip is intended for a single use, and is generally disposed of once removed.

The strip of the present invention may be impregnated with various substances to further function as a substance delivery system. As indicated, the strips can be infused with a breath freshener, fluoride, teeth whitener, flavoring, or medication, such as a topical anesthetic to relieve pain, an anticoagulant to prevent bleeding, or an antibiotic to prevent infection.

The substances could be mixed with the wax or other pliable substance forming the body of the strip, or infused into the thin film material forming the top face of the strip, or may be micro-encapsulated in the body or top face of the strip, so that movement or pressure selectively ruptures micro-capsules, already known in the art, containing the desired substance.

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

What is claimed is:

1. A shield configured to protect the mouth tissue of a user from an installed orthodontic appliance having a length, comprising:

a rectilinear strip comprising a body having a length, a width, a generally uniform thickness, first and second ends, and first and second sides, said body comprising a formable material which is generally form-stable at room temperature and sufficiently pliable at an elevated temperature to be conformed to said orthodontic appliance, said material having situated between said first and second sides reinforcement means along the length of said body for promoting strength, said first side of said body further comprising a layer of smooth, generally fluid impermeable material configured to communicate with the mouth tissue of the user, said second side of said body exposing said formable material to allow for direct application to said orthodontic appliance.

2. The mouth shield system of claim 1, wherein said material forming said body comprises wax.

3. The mouth shield system of claim 2, wherein said reinforcement means comprises a layer of mesh.

4. The mouth shield system of claim 3, wherein said smooth, generally fluid impermeable material comprising said first side of said body comprises a plastic film sheet.

5. The mouth shield system of claim 1, wherein said material is infused with a flavoring substance.

6. The mouth shield system of claim 1, wherein said material is infused with medication.

7. The mouth shield system of claim 1, wherein said material is infused with a tooth strengthening substance.

8. A mouth shield, comprising:

a generally flat, elongated strip comprising a body having a length, a width, a generally uniform thickness, first and second ends, and first and second sides, said length of said body greater than said width of said body, said body comprising a formable material which is generally form-stable at room temperature and pliable at an elevated temperature, said material having situated between said first and second sides reinforcement means along the length of said body for promoting strength, said first side of said body further comprising a layer of smooth, generally fluid impermeable material configured to communicate with the mouth tissue of the user, said second side of said body exposing said formable material so as to allow engagement of said formable material to said orthodontic appliance.

9. The mouth shield system of claim 8, wherein said material is infused with a flavoring substance.

10. The mouth shield system of claim 8, wherein said material is infused with medication.

11. The mouth shield system of claim 8, wherein said material is infused with a tooth strengthening substance.

12. The method of isolating an orthodontic appliance having a length from the mouth tissue of a user, comprising the steps of:

a. Providing a strip comprising a body having a length, a width, a generally uniform thickness, first and second ends, and first and second sides, said body comprising a material which is generally form-stable at room temperature and sufficiently pliable at an elevated temperature to be conformed to said orthodontic appliance, said material having situated between said first and second sides reinforcement means along the length of said body for promoting strength, said first side of said body further comprising a layer of smooth, generally fluid impermeable material configured to communicate with the mouth tissue of the user, said second side of said body configured to engage said orthodontic appliance;

b. Longitudinally aligning said strip with the length of said orthodontic appliance, facing said second side of said body towards said orthodontic appliance, and said first side of said body away from said orthodontic appliance;

c. Applying said second side of said strip to said orthodontic appliance, enveloping said second side of said strip about an exposed portion of said orthodontic appliance;

d. Allowing said second side of said strip to communicate with the mouth tissues of said user, isolating said orthodontic appliance from said mouth tissues.

13. The method of claim 12, wherein there is further included in step "b" the step of warming said strip, rendering said body pliable.

14. The method of claim 12, wherein in step "a" said body of said strip is infused with medication, and in step "d" there is further included the step of said medication diffusing, via said body of said strip, into said mouth.

15. The method of claim 12, wherein in step "a" said body of said strip is infused with flavoring, and in step "d" there is further included the step of said medication diffusing, via said body of said strip, into said mouth.

16. The method of claim 12, wherein in step "a", said material forming said body comprises wax, said reinforcement means comprises mesh, and said smooth, generally fluid impermeable material comprises plastic film.

* * * * *